United States Patent
Anthone

(10) Patent No.: US 6,811,553 B2
(45) Date of Patent: Nov. 2, 2004

(54) METHOD AND INSTRUMENT FOR CATARACT SURGERY

(76) Inventor: Kenneth D. Anthone, 4152 Coventry Green Cir., Williamsville, NY (US) 14221

( * ) Notice: Subject to any disclaimer, the term of this patent is extended or adjusted under 35 U.S.C. 154(b) by 0 days.

(21) Appl. No.: 10/291,343

(22) Filed: Nov. 8, 2002

(65) Prior Publication Data

US 2003/0093099 A1 May 15, 2003

Related U.S. Application Data

(60) Provisional application No. 60/338,138, filed on Nov. 9, 2001.

(51) Int. Cl.$^7$ ................................. A61F 9/00
(52) U.S. Cl. ..................................... 606/107
(58) Field of Search ............................. 606/107, 161, 606/166; 623/6.11, 6.12

(56) References Cited

U.S. PATENT DOCUMENTS

| | | | |
|---|---|---|---|
| 2,117,312 A | * | 5/1938 | Gauly .................. 606/107 |
| 4,579,116 A | * | 4/1986 | Catalano .............. 606/107 |
| 4,676,793 A | | 6/1987 | Bechert, II |
| 5,057,098 A | | 10/1991 | Zelman |
| 5,156,607 A | | 10/1992 | Kansas |
| 5,217,459 A | | 6/1993 | Kamerling |
| 5,451,230 A | | 9/1995 | Steinert |
| 5,653,724 A | | 8/1997 | Imonti |
| 5,993,408 A | | 11/1999 | Zaleski |

OTHER PUBLICATIONS

K. D. Anthone, "Surgeon: Crack–and–Stack Supracapsular Method is Safe," Ocular Surgery News, Oct. 1, 2001, vol. 18, No. 19, pub. by Slack Incorporated of Thorofare, NJ.

* cited by examiner

Primary Examiner—Kevin T. Truong
(74) Attorney, Agent, or Firm—James C. Simmons

(57) ABSTRACT

A method to provide an efficient, safe, and easy to use supracapsular method for removal of cataracts, wherein a groove is formed in the cataract nucleus, the nucleus is cracked along the groove into two halves and rotated approximately 90 degrees, force is applied to the proximal half to effect movement of the distal half into a stacked position relative to the proximal half, and the nucleus halves along with the remainder of the cataract are then emulsified and removed.

In order to minimize the chances of trauma to the capsule while sweeping the lens capsule away from cataract portions as well as making a crack in the nucleus and for otherwise assisting in manipulation of nucleus portions, an instrument has a prongless cataract-engaging portion, preferably with a convex frontal edge.

20 Claims, 5 Drawing Sheets

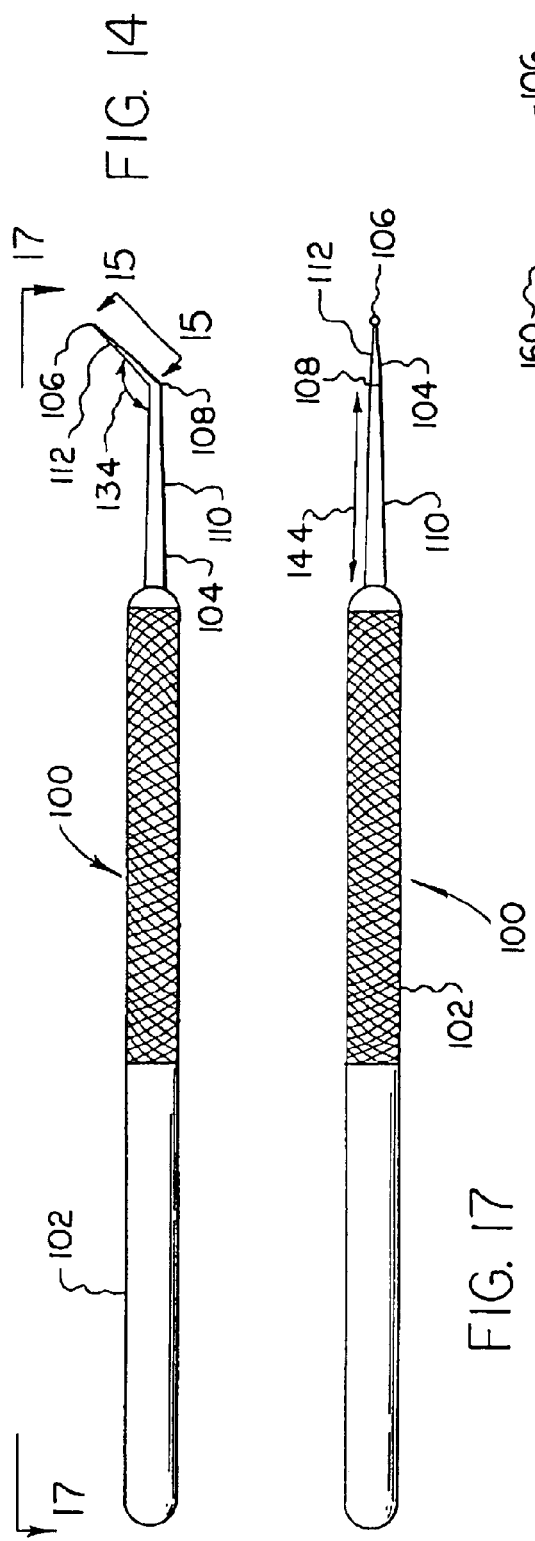
FIG. 14
FIG. 17
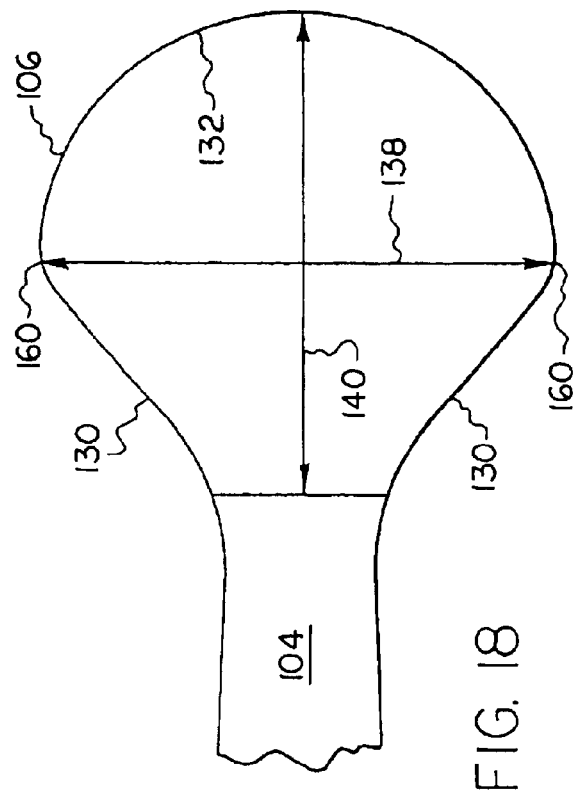
FIG. 18

METHOD AND INSTRUMENT FOR CATARACT SURGERY

Priority of U.S. provisional patent application Ser. No. 60/338,138, filed Nov. 9, 2001, the disclosure of which is hereby incorporated herein by reference, is hereby claimed.

The present invention relates generally to cataract surgery. More particularly, the present invention relates to a supracapsular method of cataract phacoemulsification and an instrument therefor.

A cataract refers to an area or portion of the crystalline lens of an eye that has become opaque. Usually, the cataract, which is contained within a lens capsule, comprises the hardened opaque or cloudy lens portion known as the cataract nucleus surrounded by the softer cortex. Treatment therefor involves removing a portion of the capsule to provide an opening (capsulorrhexis) and removal of the diseased lens through the opening and its replacement within the remaining portion of the capsule with an artificial lens. For the purposes of this specification and the claims, the term "cataract" refers to the entire diseased lens.

Cataract removal may be broadly classified as "supracapsular", wherein the cararact is removed from the capsule before phacoemulsification either with or without nuclear disassembly, and "intracapsular", wherein the cataract is phacoemulsified while it remains within the capsule. One supracapsular approach has involved a difficult flipping maneuver known as David Brown's "phaco flip", wherein the entire lens is "flipped" out of the capsule before phacoemulsification. Other supracapsular approaches involve tilting the lens out of the capsule. These difficult approaches include one known as Richard Lindstrom's "tilt and tumble" phaco and a technique attributed to Richard Kratz.

Because of the difficulties of the supracapsular approaches, an intracapsular approach known as the "divide and conquer" method has remained popular. In accordance with this method, referring to FIG. 1 wherein the capsule is illustrated at 20, the capsule opening or capsulorrhexis is illustrated at 22, the diseased lens or cataract is illustrated at 23, the cataract nucleus is illustrated at 24, and the cortex is illustrated at 26, a phaco tip 28 is used to make a groove 30 in the nucleus 24, the cataract rotated 90 degrees, and a second groove 32 made in the nucleus 24. The nucleus 24 is then divided into four quadrants 34 using the phaco tip 28 and a second instrument known as the Bechert nucleus rotator, which is illustrated at 36 in FIG. 13. In the use of this intracapsular method, it is difficult to position the first quadrant for emulsification. Dense cataracts often prove quite difficult to disengage because of significant resistance by the remaining three quadrants, which remain interlocked even though they have been cracked. The surgeon must move one-quarter of the entire nuclear mass against the other 75 percent, a series of maneuvers that require significant force to be directed against the resistance, particularly if residual epinuclear adhesions remain. Four discrete triangular-shaped quadrants translate into 12 pointed areas that clearly increase the potential of a capsular rent if excessive manipulation is required to engage and position each quadrant for emulsification.

It has been suggested that it is more efficient to remove the nucleus from the capsular bag prior to phacoemulsification. In addition, supracapsular methods are considered safer since capsular rupture is exceedingly rare with such methods. It is thus considered desirable to return to a supracapsular method which does not have the difficulties of the supracapsular methods discussed above.

Of interest to the present invention may be U.S. Pat. Nos. 4,676,793; 5,057,098; 5,156,607; 5,451,230; and 5,653,724, which disclose various techniques for cataract surgery and which are hereby incorporated herein by reference.

I have developed and have been successfully using for more than a year an easy to use supracapsular method of cataract removal for soft nuclear cataracts which are found in younger patients, wherein a single deep groove is formed in the nucleus (wherein the two halves remain joined after the groove is formed) and one half is "flapped" over onto the other joined half to allow supracapsular phacoemulsification to occur.

The above "flap and stack" technique does not work for harder cataracts found in older patients since the forces anchoring the two cataract portions together causes resistance to maneuverability of the distal portion. It is therefore considered desirable to provide an efficient and safe supracapsular method, which is also easy to use, for removal of harder cataracts.

The Bechert rotator 36 (FIG. 13) has been used to separate the cataract from the capsule 20 and to otherwise assist in manipulation of the nucleus portions as needed. The rotator 36 is seen to comprise a pair of prongs 38 defining a Y-shape. These prongs 38 may undesirably traumatize the capsule 20.

It is accordingly an object of the present invention to provide an efficient, safe, and easy to use supracapsular method for removal of cataracts.

It is another object of the present invention to provide an instrument for sweeping the lens capsule away from cataract portions and for otherwise assisting in manipulation of nucleus portions wherein the chances of trauma to the capsule are minimized.

In order to provide an efficient, safe, and easy to use supracapsular method for removal of cataracts, in accordance with the present invention, a groove is formed in the cataract nucleus, the nucleus is cracked along the groove into two halves and rotated approximately 90 degrees, force is applied to the proximal half to effect movement of the distal half into a stacked position relative to the proximal half, and the nucleus halves along with the remainder of the cataract are then emulsified and removed.

In order to minimize the chances of trauma to the capsule while sweeping the lens capsule away from cataract portions as well as making a crack in the nucleus and for otherwise assisting in manipulation of nucleus portions, in accordance with the present invention, an instrument is provided which has a prongless portion, preferably with a convex frontal edge, for engaging the cataract.

The above and other objects, features, and advantages will be apparent in the following detailed description of the preferred embodiments of the present invention when read in conjunction with the accompanying drawings wherein the same reference numerals denote the same or similar parts throughout the several views.

BRIEF DESCRIPTION OF THE DRAWINGS

FIG. 14 is a side view of an instrument which embodies the present invention.

FIG. 17 is a top view, taken along lines 17—17 of FIG. 14, of the instrument of FIG. 14.

FIG. 18 is a more enlarged plan view of a portion of the shank and the working part of the instrument of FIG. 14.

DETAILED DESCRIPTION OF THE PREFERRED EMBODIMENTS

Referring to FIGS. 2 to 12, there is illustrated a method of supracapsular phacoemulsification of a lens 23 containing a hard cataract 24. While the method of the present invention is described as especially useful for removing hard cataracts, which would include certain hard brunescent cataracts, it should be understood that the method may also be used for removing softer cataracts.

Figure 1:
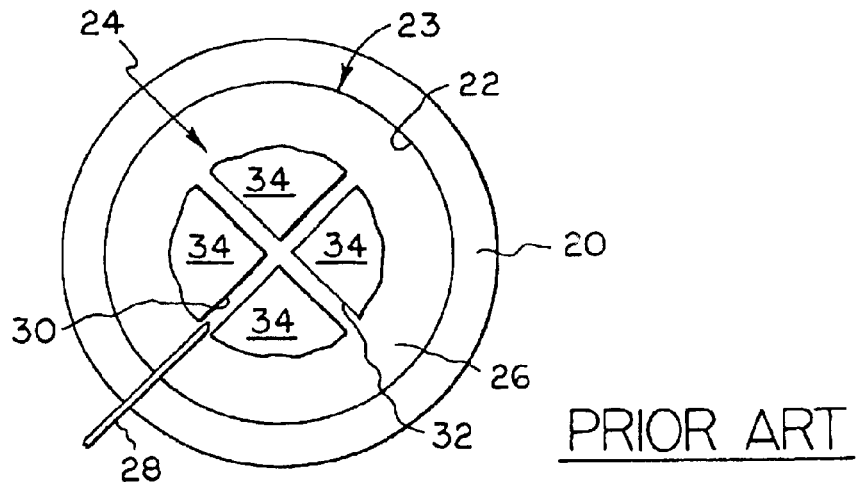
FIG. 1 is a schematic view illustrating a method of removal of a cataract from its lens capsule in accordance with the prior art.
Figure 2:
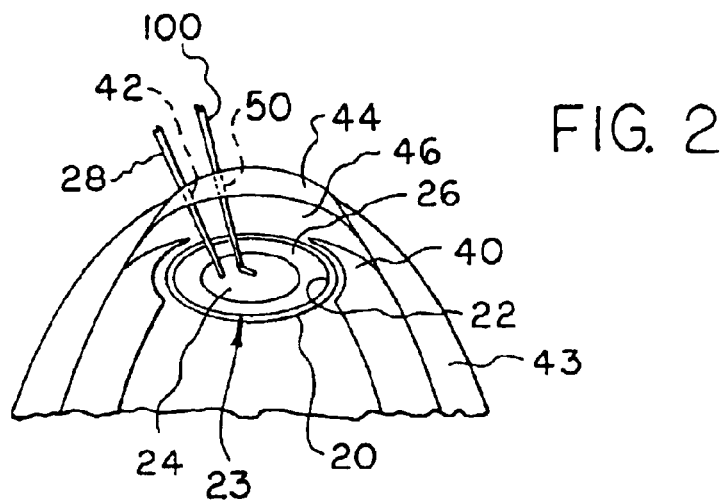
FIG. 2 is a schematic fragmentary view showing a portion of an eye containing a cataract and illustrating removal of the cataract in accordance with the present invention.
Figure 3:
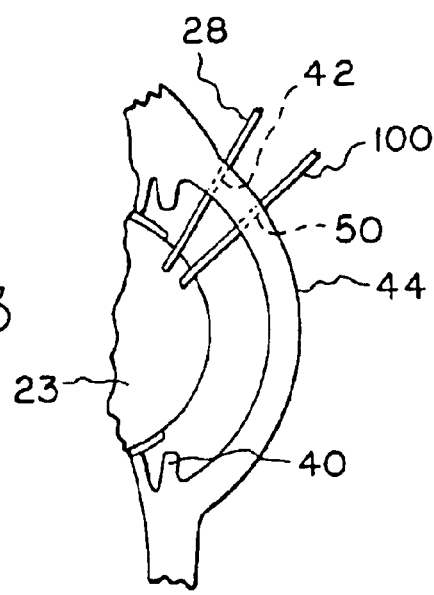
FIG. 3 is a schematic side view thereof.
Figure 4:
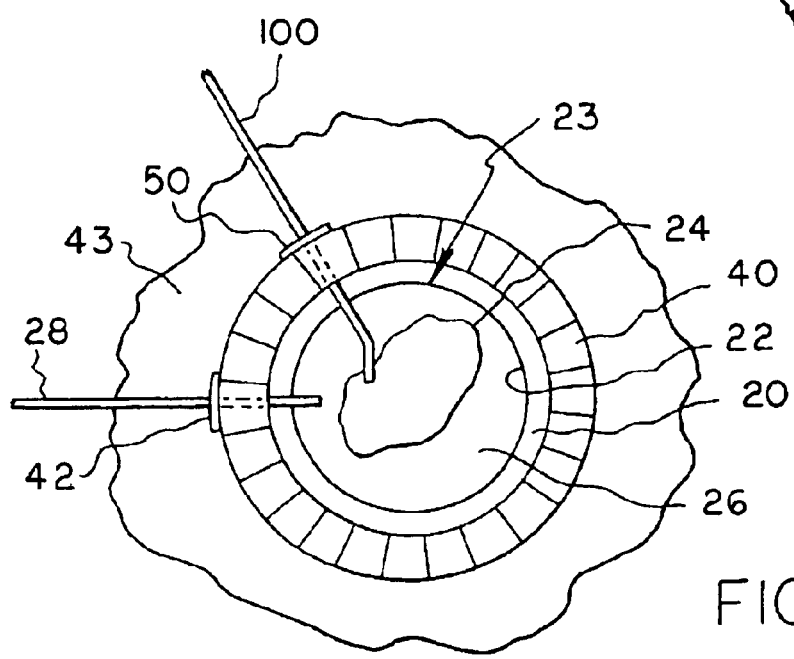
FIG. 4 is a schematic front view thereof.

After dilating the pupil 40, as illustrated in FIGS. 1 to 3, so that the iris is out of the way, an incision (clear corneal incision), illustrated at 42, of about 2.7 to 3 mm is made through the cornea 44 at the limbus or corneal-sclera junction (the sclera being illustrated at 43), and a needle (not shown) is inserted through the incision 42 to form a hole in the lens capsule 20. The anterior chamber 46 between the cornea 44 and lens capsule 20 is filled with a viscoelastic material before insertion of the needle to prevent collapse. A forceps or other suitable instrument (not shown) is then inserted through the incision 42 to peal away a portion, approximately 5 to 6 mm diameter, of the lens capsule 20 to leave opening 22 through which access may be gained to the cataract 24 and 26. With experience, the opening diameter may be decreased. Hydrodisection is instituted to cleave or separate the cataract 23 from the lens capsule 20. A second clear corneal incision, illustrated at 50, is made at about 10 to 40 degrees upwardly from incision 42 and is similar thereto, for insertion of instrument 100, which will be described in greater detail hereinafter.

Figure 5:
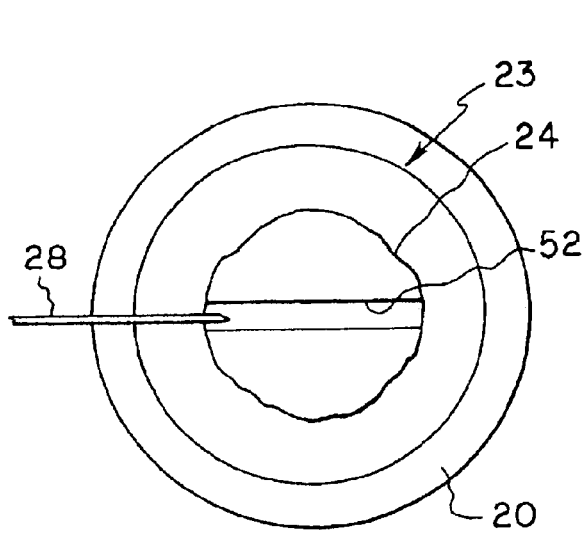
FIGS. 5 and 7 to 12 are schematic front view illustrations of a series of steps for the cataract removal.
Figure 6:
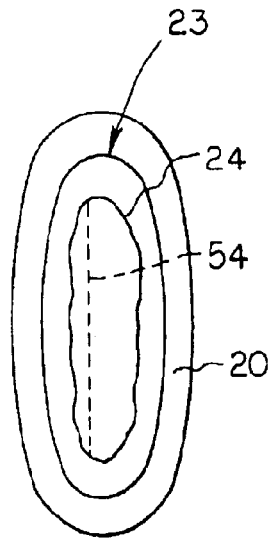
FIG. 6 is a schematic side view of the step illustrated in FIG. 5.

Referring to FIGS. 5 and 6, a conventional phacoemulsifier needle 28, which uses pedal-operated irrigation and aspiration or suction to emulsify and suck the cataract material out from the lens capsule, is inserted through incision 42 and is operated to form a single deep groove, illustrated at 52, centrally in the cataract nucleus 24 almost to the lens capsule, the bottom of the groove 52 being illustrated at 54.

Figure 7:
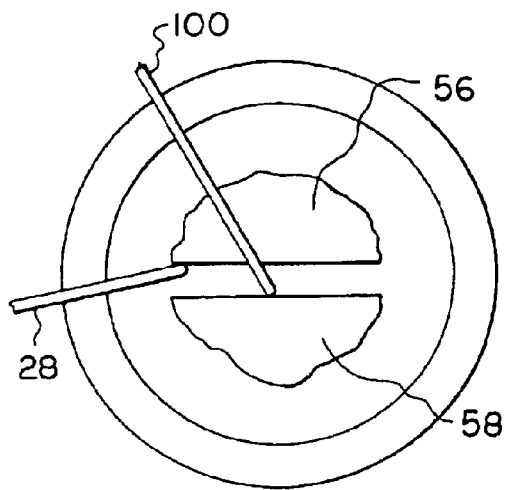
Figure 8:
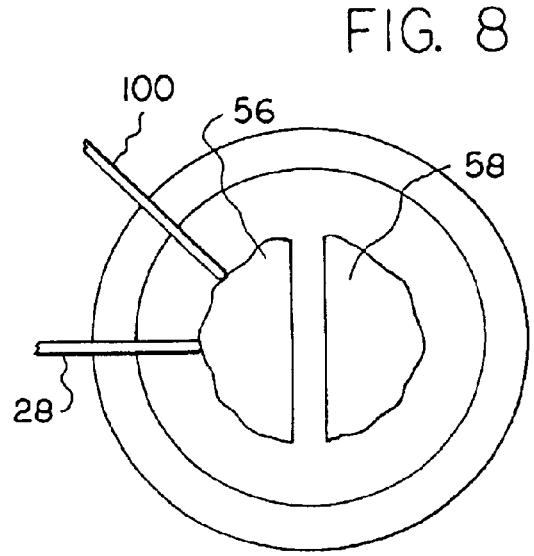

Referring to FIG. 7, in order to eliminate forces which are acting to anchor the two cataract portions together causing resistance to manueverability of the distal portion relative to the proximal portion, the instrument or enabler 100 is inserted through incision 50, and by bearing the enabler 100 on one half and the phaco tip 28 on the other half of the nucleus 24 or by otherwise suitably manipulating the instruments 28 and 100, the nucleus 24 is cracked into two discrete halves 56 and 58, as illustrated in FIG. 7. The method of the present invention, wherein only the two discrete halves 56 and 58 are formed instead of the four quadrants of the prior art method of FIG. 1, thus advantageously allows only four pointed areas to remain potential threats to the posterior lens capsule, as opposed to 12. The instruments 28 and 100 are then manipulated to effect rotation of the two halves 56 and 58 approximately 90 degrees (i.e., so that one half 56 is proximal and the other half 58 is distal), as illustrated in FIG. 8, orienting the crack horizontally. Alternatively, the nucleus 24 (with the groove 52 therein) may be first rotated then cracked into the two halves 56 and 58.

Figure 9:
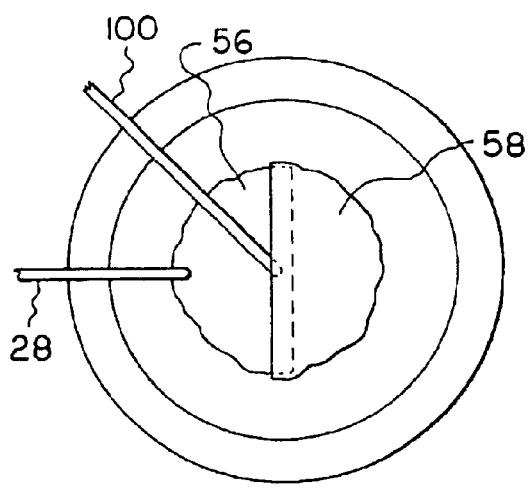
Figure 10:
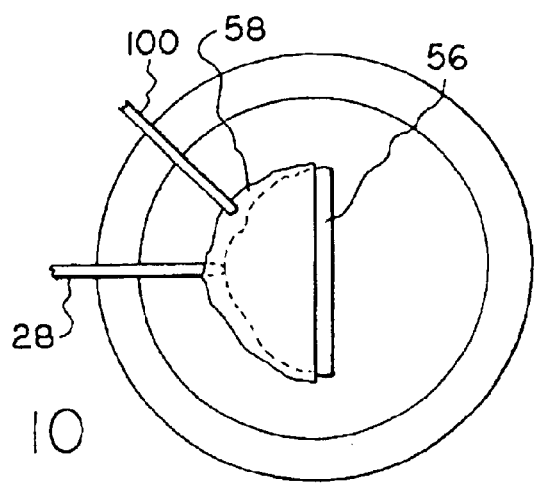

Referring to FIG. 9, the phaco tip 28 is then placed against the middle of the proximal half of the nucleus, and the foot is released from the phaco tip pedal to cause irrigation to cease, thus softening the eye and so that no resistance is offered to the stacking procedure hereinafter described. Gentle downward and forward force is then applied with the phaco tip 28 and the instrument 100 is manipulated as needed, stacking the distal half 58 in an inverted orientation over the proximal half 56. The distal half 58 then rotates or tumbles into an inverted superior position, as illustrated in FIG. 10, by folding over the proximal half 56. As seen in FIG. 10, the halves 56 and 58 are now stacked. The capsule advantageously remains safely intact because little or no pressure is exerted against the capsule by the sharper edges of the nucleus. In conventional nucleus flip techniques, the entire cataract must be inverted wherein there may disadvantageously be greater incidences of corneal edema and striae immediately postoperatively. Thus, in the method of the present invention, only one blunt half of the cataract is inverted in a controlled manner, and the short phaco tip only needs to be pushed half as far into the eye. Since only the distal half is inverted, the amount of force and manipulation required is minimized. The resulting stacked position of the nuclear halves leaves adequate room for manipulation and excellent visibility, as the phaco tip may now engage the entire nucleus in the central area of the pupil. Since no epinuclear adhesions remain, the surgeon also enjoys complete freedom of movement of both nucleus halves so that the phacoemulsification, as described hereinafter, may be faster, safer, and easier.

The halves are then emulsified using any suitable technique depending on how the cataract presents and can be done in any manner commonly known to those of ordinary skill in the art to which this invention pertains. As a golfer would state, "play it the way it lays." The following is a standard process for such emulsification. The linear vacuum level of the phaco tip 28 is raised from 50 to 100 mm Hg or other suitable level, and the supracapsular top half 58 of the nucleus is emulsified in the center, which leaves two smaller pieces which are then easily emulsified using low phaco power and higher vacuum levels.

Figure 11:
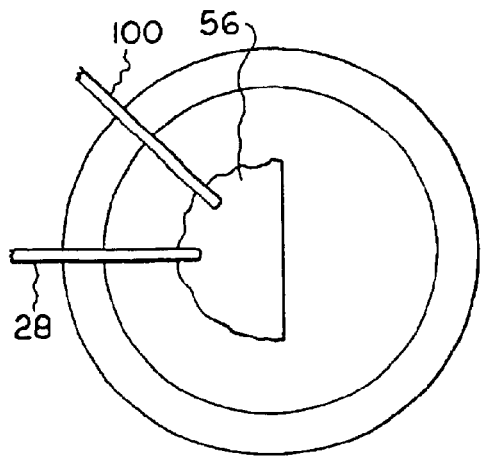

The inferior half 56 now remains in the capsule, as seen in FIG. 11, but free from epinuclear adhesions. It is easily emulsified since it should remain centered after removal of the superior half 58. If, however, it does not easily move to the center of the pupil, the phaco tip may be inserted into the middle of it and the vacuum power increased, then the half 56 pulled toward the center, or the half 56 may just be manually moved to the center with the instrument 100.

Manual movement of the inferior half 56 of the nucleus may be easier by first rotating it about 90 degrees, then taking the foot off the phaco tip pedal to cease irrigation through the phaco tip. When the proximate tip of the nucleus tilts upward, it is easily engaged by the phaco tip to bring it up to a supracapsular position. This second half 56 of the nucleus is then easily emulsified longitudinally or through its strongest central part where it may, if desired, be cracked while emulsifying.

Figure 12:
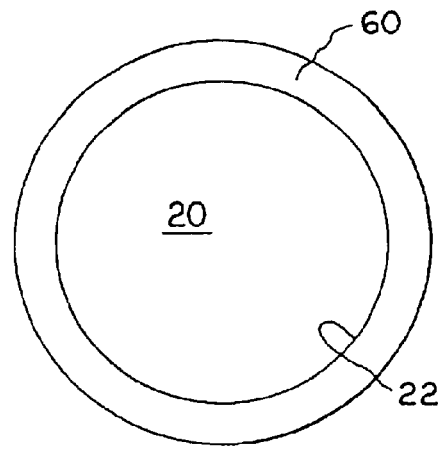

When the nucleus halves 56 and 58, including the relatively soft cortex 26, have been emulsified and removed, as illustrated in FIG. 12, an artificial lens may be inserted in the capsule opening 22 to be held in place under the anterior capsule portion 60. It should be understood that the cracked and stacked halves 56 and 58 may be emulsified and removed in any suitable way.

My use of the above crack and stack method for a period of time (which began less than a year before the filing date of the provisional application of which priority is claimed herein) has resulted in the overall complication rate being reduced by 75 percent, the average surgical time being reduced from 18 to 8 minutes, and the anterior vitrectomy rate being reduced from 1 to 0.2 percent. Thus, the method of my present invention is shown to be safer and faster, and it is also easier to use.

Figure 15:
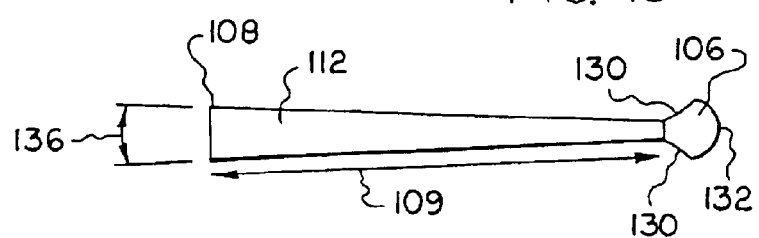
FIG. 15 is an enlarged plan view, taken along lines 15—15 of FIG. 14, of a portion of the shank and the working part of the instrument of FIG. 14.

Referring to FIGS. 14, 15, and 17, the instrument 100 includes a generally cylindrical knurled (over about half of its length) handle 102 from an end of which extends coaxially therewith a shank 104 which is of a small diameter to allow its insertion through incision 50 and to the position of the cataract. At the other end of the shank 104 is the working part 106, which will be described shortly. At a short distance from the working part 106, the shank 104 has a bend, illustrated at 108, defining a main portion 110 and a bent portion 112, in order to allow the working part 106 to be easily positioned as needed by rotation of the handle 102 along with axial movement thereof.

In addition to aiding in cracking the cataract into two halves and manipulating the cataract halves 56 and 58 into the stacked position, the instrument 100 may also be used to sweep the lens capsule 20 away from the cataract or one of the halves if it gets caught thereon. However, prongs on the Bechert rotator (FIG. 13) may tear or otherwise cause trauma to the capsule. In order to reduce the chances of trauma to the capsule particularly while sweeping it away from the cataract, the working part 106 is flat and prongless (i.e., it may be said to have the shape of a single flat paddle), it being curved along its perimetric edge so as not to have any damaging sharp points or prongs or otherwise any protrusions. The prongless paddle shape also provides greater mass so as to make the stacking procedure easier.

The cataract engaging portion 106 has a pair of side edges 130 which flare from the shank 104 outwardly from each other, and the side edges are joined by a frontal cataract-engaging edge 132. In order to efficiently achieve cracking of the cataract, the frontal edge 132 is preferably convex, as illustrated in FIG. 15, so as to provide a dome shape.

Figure 13:
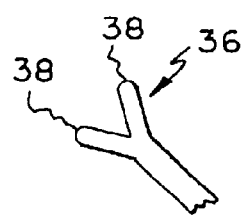
FIG. 13 is an enlarged plan view of a portion of the shank and the working part of an instrument in accordance with the prior art.

The instrument 100 is thus sized and adapted for insertion at least partially under a lens capsule of an eye (i.e., the remaining portion of the capsule after a portion is removed to provide opening 22). Its overall size may, for example, generally be similar to the size of the aforesaid Bechert nucleus rotator (which is illustrated in FIG. 13), which is marketed under the Storz Instruments brand name by Bausch & Lomb Surgical, although the Bechert nucleus rotator has a very different shape, as previously discussed.

For purposes of illustration and not for limitation, the following are exemplary dimensions for the instrument 100. The overall length of the instrument 100 may, for example, be about 120.65 mm. The diameter of the handle 102 may, for example, be about 4.76 mm. The shank 104 has a diameter at the handle 102 which may, for example, be about 1.3 mm and may taper to a diameter at the bend 108 of, for example, about 0.5 mm. The angle, illustrated at 134, at which the shank 104 is bent is greater than a right angle and less than 180 degrees, for example, between about 100 and 170 degrees, preferably between about 130 and 150 degrees, for example, about 135 degrees. The length, illustrated at 144, of the portion of the shank 104 between the handle 102 and the bend 108 is, for example, about 17.4 mm. The shank 104 tapers from the bend 108 at an angle, illustrated at 136, of, for example, about 4.44 degrees to a diameter at the cataract-engaging portion 106 of, for example, about 0.25 mm. The flat cataract-engaging portion 106 has a thickness of, for example, about 0.25 mm which merges into the conical shape of the shank 104. As long as it can be suitably inserted under the lens capsule, the larger the prongless single paddle 106 of the present invention the better, but if the paddle is too large, the size of the incision 50 may have to be increased. Accordingly, the width and height, illustrated at 138 and 140 respectively, of the cataract engaging portion 106 may each suitably be between about 0.5 and 1.5 mm, for example, each being in the range of about 0.6 to 0.9 mm and being equal to each other. While the width and height of portion 106 are described herein as equal to each other, it should be understood that its width 138 may be different from its height 140. The side edges 130 are slightly concave; they are each radiused at, for example, about 37 degrees. The convex frontal edge 132 is radiused at, for example, about 1.27 mm. The curvature, illustrated at 160, joining the frontal edge 132 to each of the side edges 130 (which are each, for example, about midway of the height 140 of the portion 106) is convex and is radiused at, for example, about 0.31 mm. Thus, the perimetric edge of the portion 106 is desirably continuous and without any damaging sharp edges all the way around. The instrument 100 is composed preferably of titanium which doesn't rust as easily as stainless steel, is not as subject to wear and tear, and should last longer. However, the instrument 100 may alternatively be made of stainless steel or other suitable material. If desired, the instrument 100 may be made to be disposable and thus made of hard plastic or other suitable material. The instrument 100 is preferably composed of a single part but, if desired, may be composed of two or more parts suitably joined.

In addition to its use for removing cataracts, the instrument 100 may also be used for implanting phakic lens for the purpose of cosmetic correction of glasses (to correct sight without using laser surgery) as well as for implanting aphakic lens. When the instrument 100 is used for implanting lens, it is preferred that the length, illustrated at 109, of the shank portion 104 be increased. Thus, depending on the preference of the user and how much the user will use the instrument for implanting lens, the instrument 100 has two different preferred lengths 109. For removing cataracts, the length 109 is preferably between about 5.5 and 7.5 mm, for example, about 6.5 mm, which is a less unwieldy length for removing cataracts. For implanting lens, the length 109 is preferably between about 6 and 10.5 mm, for example, about 8.5 mm for a phakic lens or about 8 mm for an aphakic lens. Thus, a length 109 in the range between about 6 and 7.5 mm is considered a preferred length for using the instrument both for removing cataracts and for implanting lens.

Figure 16:
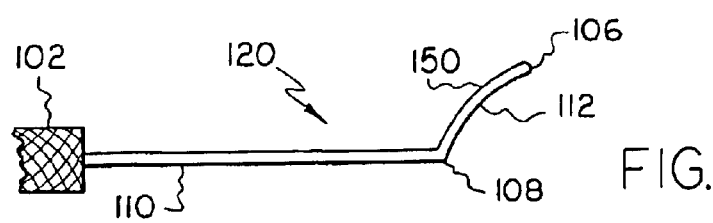
FIG. 16 is a partial view, similar to that of FIG. 14, of an alternative embodiment of the instrument.

Referring to FIG. 16, there is illustrated generally at 120 an alternative embodiment of the instrument. In order that the instrument 120 may better conform to or complement the curvature of the lens capsule curvature as the instrument 120 sweeps the capsule away from a cataract half, the upper or lens capsule-engaging surface 150 of the bent portion 112 of the shank 104 is convexly curved slightly between the bend 108 and the cataract-engaging portion 106, the curvature preferably being similar to that of a lens capsule centrally thereof.

The instrument 100 of the present invention is provided, like the Bechert nucleus rotator, to be used to (1) crack the nucleus, (2) retract the iris, (3) guide the cataract pieces into the phaco tip, and (4) assist in conventional cataract techniques including divide and conquer. However, the instrument 100 is also provided to function in other ways better than the Bechert nucleus rotator can function. Thus, the instrument 100 is also provided to be used to (5) more safely sweep the capsule away from the nucleus, (6) more easily stack the cataract pieces, (7) better protect the corneal endothelium from the top piece or otherwise, and (8) assist in intraocular lens insertion in more different ways. The instrument 100 is also provided to (9) serve as a nuclear fragment spatula such as for picking up the bottom piece, once cracked (off of the capsule). Additional uses for the instrument 100 include (10) providing traction on the (hard) nucleus to hold it in the proper position, (11) use as a cyclodialysis spatula to sweep or retract strands of vitreous material from the wound or otherwise (current cyclodialysis spatulas are undesirably pointy), (12) the ability to smash nuclear fragments into irrigation/aspiration tips better than conventional instruments therefor can do, (13) assisting in intraocular lens removal in order to replace them, (14) flipping inverted (incorrectly inserted) implants into correct position, and (15) removal or cortical shells (which are between the nucleus and the cortex). In addition, as previously discussed, the instrument 100 may also be used to (16) implant and explant phakic lens in order to correct sight without using laser surgery. The instrument 100 is thus provided with a flat single paddle shape (without prongs or sharp points) to advantageously safely minimize trauma to the lens capsule while also allowing easier stacking of nucleus halves due to its greater mass.

In view of the above 16 uses of the instrument 100 of the present invention, the instrument 100, with its (1) prongless shape with no sharp edges or points, (2) its dome-shaped forward edge to better achieve cracking, and (3) its flat single paddle shape, can eliminate (be used instead of) and is provided to function better than the following 3 instruments:

1. Bechert rotator (the rotator undesirably has prongs, as illustrated in FIG. 13 and as discussed hereinbefore).
2. Forceps for inserting implants (the instrument 100 functions better because it insures implantation of trailing loop of implant into capsular bag by "dialing" the implant).
3. Cyclodialysis spatula (the instrument 100 is not undesirably pointy as current cyclodialysis spatulas are).

It should be understood that, while the present invention has been described in detail herein, the invention can be embodied otherwise without departing from the principles thereof, and such other embodiments are meant to come within the scope of the present invention as defined by the appended claims.

What is claimed is:

1. An instrument for assisting in cataract removal comprising a handle, a shank, and a flat paddle-shaped prongless portion adapted for insertion at least partially under a lens capsule of an eye for manipulating cataract portions including pushing cataract portions into a stacked position and for sweeping a lens capsule away from cataract portions during the stacking thereof.

2. An instrument according to claim 1 wherein said shank is formed to define a first portion and a second portion to which said prongless portion is attached, said second shank portion extending at an angle relative to said first shank portion of between about 100 and 170 degrees.

3. An instrument according to claim 2 wherein said second shank portion is convex relative to said first shank portion.

4. An instrument according to claim 2 wherein said angle is between about 130 and 150 degrees.

5. An instrument according to claim 2 wherein said second shank portion has a length between about 6 and 7.5 mm.

6. An instrument according to claim 2 wherein said second shank portion has a length between about 5.5 and 7.5 mm.

7. An instrument according to claim 2 wherein said second shank portion has a length between about 6 and 10.5 mm.

8. An instrument according to claim 1 wherein said prongless portion has a pair of side edges and a convex frontal edge extending between said side edges.

9. An instrument according to claim 7 wherein said side edges flare from said shank outwardly from each other.

10. An instrument comprising a handle, a prongless cataract engaging portion, and a shank extending between said handle and said cataract engaging portion, said cataract engaging portion having a pair of side edges and a convex frontal edge extending between said side edges, said shank having a first portion and further having a second portion from which said cataract engaging portion extends, said shank and said cataract engaging portion sized to effect placement of said cataract engaging portion at least partially under a lens capsule of an eye for engaging a cataract and for manipulating cataract portions to assist in removal thereof, and said cataract engaging portion being co-axial with said second shank portion.

11. An instrument according to claim 10 wherein said second shank portion extends at an angle relative to said first shank portion of between about 100 and 170 degrees.

12. An instrument according to claim 11 wherein said second shank portion is convex relative to said first shank portion.

13. An instrument according to claim 11 wherein said angle is between about 130 and 150 degrees.

14. An instrument according to claim 10 wherein said side edges flare from said shank outwardly from each other.

15. An instrument according to claim 1 wherein said prongless portion has a thickness which is about 0.25 mm.

16. An instrument according to claim 10 wherein said prongless portion is a flat paddle-shaped portion.

17. An instrument for assisting in cataract removal comprising a handle, a shank, and a prongless portion adapted for insertion at least partially under a lens capsule of an eye for manipulating cataract portions including pushing cataract portions into a stacked position and for sweeping a lens capsule away from cataract portions during the stacking thereof, said shank having a first portion and further having a second portion from which said prongless portion extends, and said prongless portion being co-axial with said second shank portion.

18. An instrument according to claim 17 wherein said prongless portion is a flat paddle-shaped portion.

19. An instrument according to claim 17 wherein said prongless portion has a thickness which is about 0.25 mm.

20. An instrument according to claim 17 wherein said second shank portion extends at an angle relative to said first shank portion of between about 100 and 170 degrees.

* * * * *